United States Patent [19]

Hartwell et al.

[11] Patent Number: 4,719,923
[45] Date of Patent: Jan. 19, 1988

[54] NON-INVASIVE BLOOD FLOW MEASUREMENTS UTILIZING AUTOREGRESSIVE ANALYSIS WITH AVERAGED REFLECTION COEFFICIENTS

[75] Inventors: Walter T. Hartwell, St. Charles; Gustavus H. Zimmerman, III, Westmont, both of Ill.

[73] Assignee: American Telephone and Telegraph Company, AT&T Bell Laboratories, Murray Hill, N.J.

[21] Appl. No.: 730,487

[22] Filed: May 6, 1985

[51] Int. Cl.$^4$ .............................................. A61B 5/02
[52] U.S. Cl. ..................................... 128/663; 364/417
[58] Field of Search ................................ 128/660–663; 73/599, 602; 364/415–417

[56] References Cited

U.S. PATENT DOCUMENTS

| | | | |
|---|---|---|---|
| 4,109,647 | 8/1978 | Stern et al. | 128/2.05 |
| 4,182,173 | 1/1980 | Papadofrangakis et al. | 73/194 |
| 4,217,909 | 8/1980 | Papadofrangakis et al. | 128/663 |
| 4,257,278 | 3/1981 | Papadofrangakis et al. | 73/861.25 |
| 4,265,126 | 5/1981 | Papadofrangakis et al. | 73/861.25 |
| 4,320,765 | 3/1982 | Cathignol et al. | 128/663 |
| 4,324,258 | 4/1982 | Huebscher et al. | 128/663 |
| 4,327,739 | 5/1982 | Chmiel et al. | 128/663 |
| 4,476,874 | 10/1984 | Taenzer et al. | 128/663 |
| 4,542,744 | 9/1985 | Barnes et al. | 128/660 |

FOREIGN PATENT DOCUMENTS

0081045  9/1982  European Pat. Off. .

OTHER PUBLICATIONS

"Computer Based Pattern Recognition of Carotid Artery Doppler Signals for Disease Classification: Prospective Validation", Y. E. Langlois, et al., *Ultrasound in Med. & Biol.*, 1984, vol. 10, No. 5, pp. 581–595.

"Analysis and Automatic Classification of Breath Sounds", A. Cohen, et al., *IEEE Transactions on Biomedical Engineering*, Sep., 1984, vol. BME-31, No. 9, pp. 585–590.

"Flow Velocity Patterns in the Carotid Bifurcations of Young, Presumed Normal Subjects", D. J. Phillips, et al., *Ultrasound in Med. & Biol.*, 1983, vol. 9, No. 1, pp. 39–49.

*Primary Examiner*—William E. Kamm
*Assistant Examiner*—Francis J. Jaworski
*Attorney, Agent, or Firm*—John C. Moran

[57] ABSTRACT

A system for non-invasively determining the amount of blood flow within an internal patient blood vessel by performing an autoregressive analysis of Doppler shifted acoustical signals resulting from the reflection of ultrasonic signals due to blood cell movement by averaging the reflection coefficients and residual energy levels resulting from the autoregressive analysis over a number of cardiac cycles. The reflection coefficients result from a linear predictive code analysis, and the term "reflection coefficients" is not used in the customary manner as defined for ultrasonic flow analysis of blood as defining a level of reflected acoustic energy. Each cardiac cycle is determined by an analysis of the patient's electrocardiogram signals, and the resulting cardiac cycles are divided into a predefined number of time segments or channels. An autoregressive analysis is then performed on each individual channel to determine the reflection coefficients and the residual energy level for each channel. The reflection coefficients and residual energy level for each particular channel are then averaged over all the cardiac cycles to obtain an averaged reflection coefficient and averaged residual energy level for each combined channel. The power spectrum for each combined channel is then calculated from the averaged reflection coefficients and averaged residual energy level and displayed on a channel-by-channel basis utilizing different colors to represent the different power levels. The utilization of different colors greatly enhances the usability of the display by medical personnel making diagnostic decisions regarding the amount of blood flow.

17 Claims, 9 Drawing Figures ulpc.c PROGRAM cspect SUBROUTINE

NON-INVASIVE BLOOD FLOW MEASUREMENTS UTILIZING AUTOREGRESSIVE ANALYSIS WITH AVERAGED REFLECTION COEFFICIENTS

CROSS-REFERENCE TO RELATED APPLICATIONS

The following applications were filed concurrently with this application:

C. M. P. Kierney, et al., case 1—1, "Non-Invasive Blood Flow Measurements Utilizing Cardiac Cycle Synchronization", Ser. No. 730,456, and is assigned in part to the same assignee as this application; and D. P. Prezas, et al., case 3—3, now U.S. Pat. No. 4,616,659 and is assigned to the same assignee as this application.

MICROFICHE APPENDICES

Included in this application are microfiche Appendices A, B, C, D and E. The total number of microfiche is 5 sheets and the total number of frames is 43.

TECHNICAL FIELD

This invention pertains to the measurement of blood flow by the analysis of Doppler shifted ultrasonic signals. In particular, the invention relates to analyzing ultrasonic signals utilizing autoregressive techniques in conjunction with synchronizing electrocardiogram (EKG) signals by averaging reflection coefficients resulting from the autoregressive analysis over a number of cardiac cycles.

BACKGROUND OF THE INVENTION

Due to the large number of deaths and physical disabilities arising from diseases of the heart and major blood vessels in both adults and children, there exists a well-recognized need for reliable, accurate, and inexpensive blood flow measurement techniques. There are two general types of methods for measuring blood flow in humans—invasive and non-invasive techniques. Since the invasive methods involve radioactivity and injections, only one study is performed per patient, and this method is not suitable for utilization as a diagnostic screening technique. There are two types of non-invasive blood flow measurements: Doppler flow meter and plethysmography. The plethysmography method involves the compression of the neck veins and is of little practical use for diagnostic screening.

The Doppler method is the most commonly used non-invasive method for performing blood flow analysis and can be repeated as necessary. In general, this method involves the transmission of an ultrasound signal through the skin to a blood vessel and the detection of the Doppler shift in the reflected ultrasound signal resulting from the movement of the red blood cells. The Doppler shifted ultrasound signal is then utilized to determine the velocity of blood flow. The latter determination is complicated due to the presence of noise in the Doppler shifted signal, and because there are sets of blood cells moving at different velocities. Each of these sets of blood cells gives rise to a different frequency shift resulting in a Doppler shifted signal that is a complex wave. One example of noise that is present in the Doppler shifted signal is that due to the movement of blood vessel walls. The wall of a blood vessel moves out during the systole portion and returns during the distole portion of the cardiac cycle. These movements result in both low- and high-frequency noise components in the Doppler shifted signal.

Yet another problem that arises in attempting to determine the amount of blood flow from the Doppler shifted signals is that the heart rate varies not only from person to person, but within a given person over a relatively small number of cardiac cycles. This variation makes the interpretation of the resulting Doppler shifted signals difficult since the difference in cardiac cycles must be included if the blood flow information is to be extracted from the Doppler shifted signal since the resulting display from these signals can have a very different appearance.

Because of the complexity of the Doppler shifted signal, the presence of noise in the Doppler shifted signal, and the variation in cardiac cycles, it is necessary to perform analog or digital analysis of these signals in order to present the information in a manner which is useful to medical personnel attempting to diagnose blood flow rate. The copending application of C. M. P. Kierney, et al., discusses three major prior art techniques that are utilized to analyze these signals: zero crossing method, phase lock loop (PLL) method, and spectra analysis method utilizing Fourier analysis.

The Kierney application discloses the utilization of autoregressive analysis techniques for analyzing these signals. The method disclosed in Kierney is responsive to Doppler shifted signals and EKG signals for a plurality of cardiac cycles to precisely determine the start and the end of each cardiac cycle. The Doppler shifted signals for each cycle are then divided into a predetermined number of time segments or channels, and an autoregressive analysis is performed on each time channel. The result of this autoregressive analysis on each channel is a power spectrum for each channel of all cardiac cycles resulting in a large amount of data. These power spectra are then averaged on an individual channel basis over all cycles, and the result is presented on a color display with each color representing a particular power level at a given frequency and time segment.

The Kierney method presents to medical personnel an accurate and easy to diagnose display of the blood flow within a patient's blood vessel, and the method is superior to the prior art techniques. Kierney does require that a large number of power spectrum calculations be performed since these calculations are performed for every channel of every cardiac cycle. This results in a large number of calculations. In addition, after the power spectra are averaged over all channels and cycles, a large amount of data is still required to represent the results of the test. This data must either be immediately transferred to a hardcopy via a peripheral device or stored on secondary storage devices such as magnetic disk memories. In large clinical screening centers having access to large scale storage devices and a plurality of hard copy output devices, this large amount of data generated by the Kierney method does not present any particular problems. However, in small medical multiphase screening laboratories, the requirement of either having to immediately process and average data over a large number of cycles and plot the resulting power spectra on a hard copy device or to store all of the resulting power spectras requires computer power and peripheral devices not always available in those type of laboratories.

Therefore, there exists a need for a technique utilizing autoregressive analysis which does not require the calculation of the power spectra for each channel of every cycle and which results in a minimum amount of data so that the resulting data can be efficiently stored in computer data bases on a individual patient basis.

SUMMARY OF THE INVENTION

In an illustrative method and structural embodiment, a departure in the art is achieved by performing an autoregressive analysis of reflected Doppler shifted ultrasonic signals resulting from the blood cell movement to determine the amount of flow by averaging the reflection coefficients and residual energy levels resulting from the autoregressive analysis. Each cardiac cycle of a patient is divided into a predefined number of time segments or channels by first determining the start and the end of each cardiac cycle from the patient's electrocardiogram signals. An autoregressive analysis is then performed on each individual channel to determine the reflection coefficients and the residual energy level for each channel. The reflection coefficients resulting from the autoregressive analysis closely model the blood flow within the patient's internal blood vessel and can be performed in an economical manner. The residual energy represents energy not accounted for by that modeling. The reflection coefficients and residual energy level for individual channels are then averaged over all of the cycles resulting in a small amount of data that represents the blood flow within the patient's blood vessel. These averaged reflection coefficients and residual energy levels can then be stored in economical mass storage devices for later analysis and display. For interpretation by medical personnel, the reflection coefficients and residual energy level data are utilized to calculate averaged power spectra for individual averaged channels. Advantageously, these averaged power spectra are then displayed on a channel basis using different colors to represent different power levels thus greatly enhancing the ease of interpretation by medical personnel.

Advantageously, an autoregressive analysis system for obtaining the average power spectrum of a plurality of signal groups each comprising a plurality of information signals functions by a first set of program instructions determining the start and end of each of set signal groups, and a second set of program instructions is responsive to the information signals of each group for calculating reflection coefficients. A third set of program instructions is responsive to the information signals and the reflection coefficients for a given group to generate a residual energy level for each group. After all of the reflection coefficients and residual energy levels for all the groups have been calculated, a fourth set of program instructions computes the average of the reflection coefficients and the average of the residual energy levels over all the groups. A fifth set of program instructions is responsive to the averaged reflection coefficients and averaged residual energy level for generating an average power spectrum.

Advantageously, the autoregressive analysis system utilizes a Doppler shifted flow meter to transmit a beam of ultrasonic frequency acoustical waves into an internal patient vessel and for receiving the reflected acoustical echoed signal back from moving blood cells within the internal patient vessel and determining the difference between the transmitted and received signals. An analog-to-digital (ADC) converter is used to convert the sampled difference signals into digitized signals which are the information signals of the signal groups.

In addition, an electrocardiogram instrument is used to obtain the patient's electrocardiogram signals, and a second ADC converter digitizes the electrocardiogram signals. The first set of program instructions is responsive to the digitized electrocardiogram signals for determining the start and end of the signal groups which correspond to the start and end of cardiac cycles.

Advantageously, the second set of program instructions which calculates the reflection coefficients comprises three subsets of program instructions. The first subset of program instructions computes a forward error between each of the information signals of each signal group and subsequent ones of the information signals of the same group, and a second subset of programmed instruction computes backward error signals for each of the information signals of each group representing the difference between each information signal and the preceding information signals of the same group. Finally, the third subset of program instruction computes the reflection coefficients in response to the backward and forward error signals for each of the groups.

A method for determining the amount of blood flow by utilization of a system comprising a Doppler flow meter, electrocardiogram instrument, analog-to-digital converters, and a digital computer performs the following steps: determines the start and end of a patient's cardiac cycles in response to electrocardiogram signals by an analysis of digitized signals from the electrocardiogram instrument, digitizing Doppler shifted signals from the flow meter by utilization of an analog-to-digital converter, dividing the resulting digitized Doppler shifted signals into a predefined number of time channels, calculating reflection coefficients for each of said channels for said Doppler shifted signals, computing residual energy level in response to the calculated reflection coefficients and the Doppler shifted signals for each of said channels, averaging the reflection coefficients and the residual energy levels for particular channels over all of the cardiac cycles, and calculating the power spectrum from the averaged reflection coefficients and averaged residual energy level for each channel.

Advantageously, the method further comprises the steps of normalizing the average power spectrum for each of the combined channels and displaying the normalized power spectrum for each channel utilizing different colors to represent the different power levels thus enhancing the display for the ease of medical personnel performing an analysis of the amount of blood flow.

DETAILED DESCRIPTION

Figure 1:
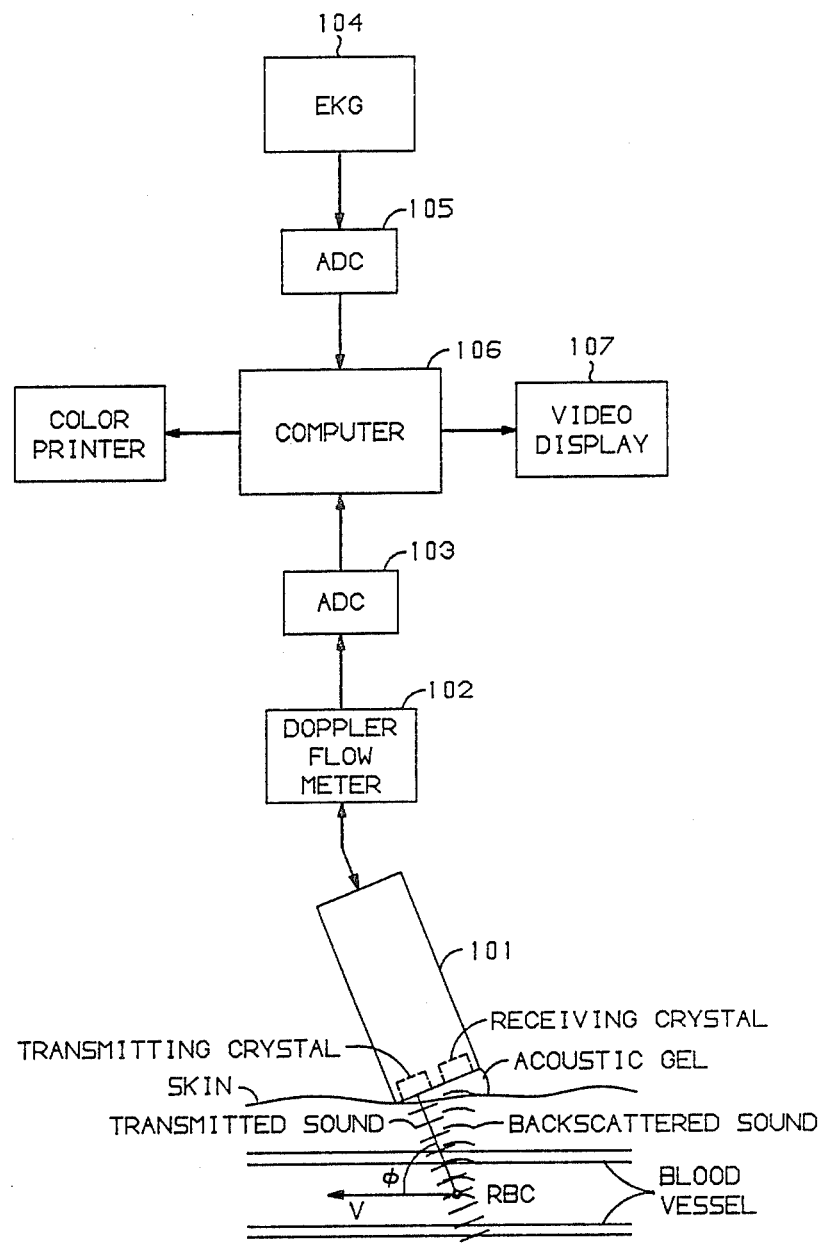
FIG. 1 illustrates, in block diagram form, a blood flow analysis system in accordance with this invention.

A system for analyzing and displaying the flow of blood within a blood vessel is illustrated in FIG. 1. Doppler flow meter 102 and ultrasonic transducer 101 generate an analog Doppler shifted signal that corresponds to the speed of the red blood cells (RBC) that are moving in a blood vessel. The frequency of the signal indicates the speed at which the blood cells are moving, and the power observed at a particular frequency indicates the number of blood cells moving at that frequency. Because of such factors as the angle of the probe and other complex physical factors, the energy does not literally correspond to the number of red cells. However, the energy is roughly proportional to the number of cells moving at any given speed.

The Doppler shifted signal is converted to digital form by analog-to-digital converter 103. Initially, computer 106 is responsive to the digitized Doppler shifted signal to store the signals along with the digitized EKG signal from electrocardiogram unit 104. After the information for a number of cardiac cycles has been stored, computer 106 is responsive to the digitized Doppler shifted signals and the digitized EKG signals to calculate the spectral power present at the various frequencies, to obtain the average of the spectral power for a number of cycles together, and to display this average spectral power over the time required for one cycle.

Figure 2:
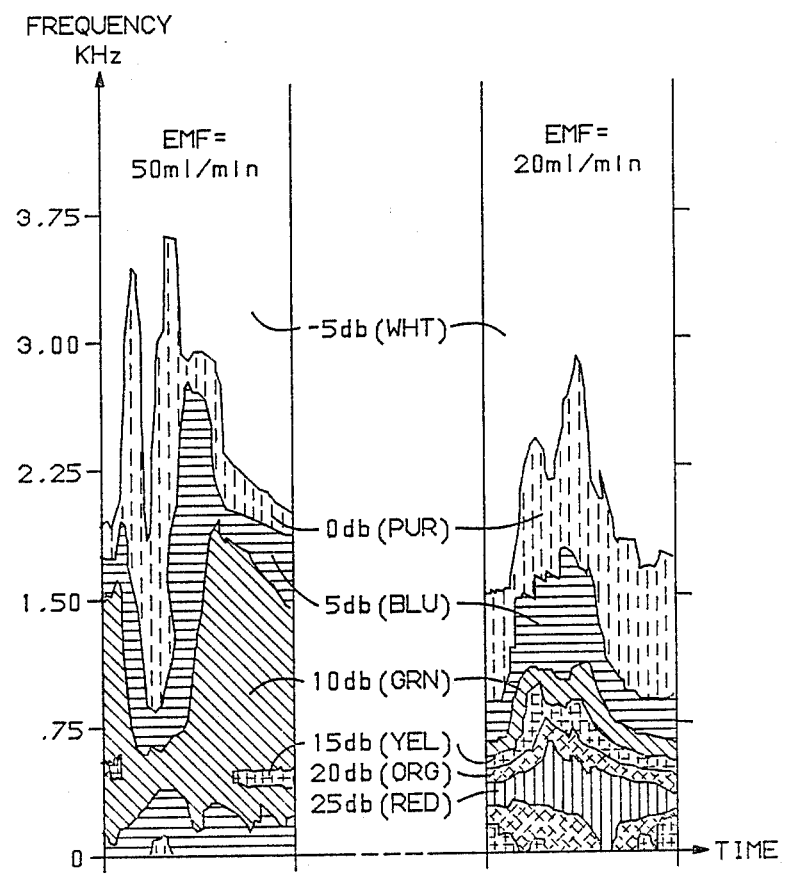
FIG. 2 illustrates in graphic form, the results of analysis performed by the blood flow system illustrated in FIG. 1 by averaging the reflection coefficients and residual energy that model the flow of blood within an artery of a piglet.

FIG. 2 illustrates the information that is displayed by computer 106 in analyzing the blood flow. Illustrated in FIG. 2 are the results of two tests performed on a piglet weighing approximately 4.2 kilograms and whose blood flow was artificially controlled. The blood flow rate was also monitored using electromagnetic flow meter that required surgical procedures and the results of the electromagnetic flow meter (EMF) are shown in the upper portion of each cycle of FIG. 2. The difference between a flow rate of 50 milliliters per minute and a flow rate of 20 milliliters per minute, as determined by the EMF meter, is quite apparent in FIG. 2 and readily discernible by medical personnel. Each test is divided into a number of time segments referred to as channels; and illustratively, there by be 50 channels per cardiac cycle.

The display illustrates the average of the power on a per-channel basis for a plurality of cycles by first determining the reflection coefficients and the residual energy by utilizing autoregressive analysis techiques for each cycle, averaging the reflection coefficients and residual energy for individual channels for all of the cycles, and then determining the power level for each individual channel from the averaged reflection coefficients and averaged residual energy as calculated using linear predictive code (LPC) analysis techniques. The term "reflection coefficients" are entities calculated during LPC analysis and are not equivalent to terms referring to a level of reflected acoustic energy as is common in blood flow analysis using ultrasonic methods. The display illustrated in FIG. 2 is produced by accurately determining the start of each cardiac cycle and the end of the cycle by analyzing the EKG signals from the patient. Once the start and end of the cardiac cycle is determined, then the digitized Doppler shifted signals in this time period are illustratively divided up into 50 channels. An autoregressive analysis is performed on all of the Doppler shifted signals in a given channel to determine the reflection coefficients and residual energy of that channel. Some implementations of autoregressive analysis are the maximum entropy method of Berg or the Durbin Levinson Recursions on Autocorrelation Coefficients method. After all of the channels for one cycle have been processed, then the next cycle is processed. When all of the reflection coefficients and residual energies for all of the channels of all of the cardiac cycles have been determined, the average of the reflection coefficients and the residual energies of individual channels of all of the cycles is taken. Finally, the power spectrum for each individual averaged channel is determined from the averaged reflection coefficients and residual energies for that channel and the resulting power spectra of the average channels is then displayed with different colors representing different power levels.

Figure 3:
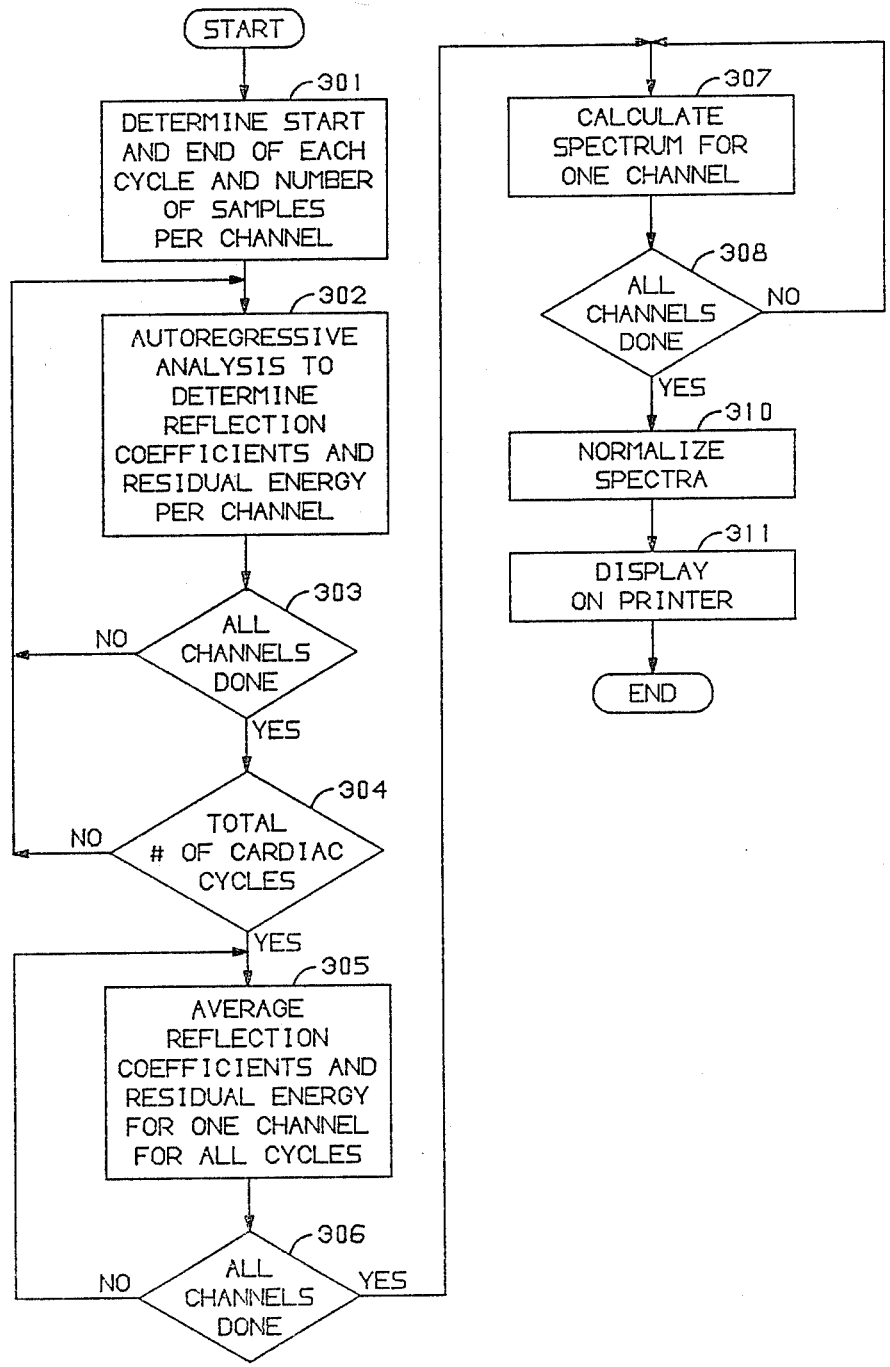
FIG. 3 illustrates, in flowchart form, the programs executed by computer 106 of FIG. 1 in performing the blood flow analysis.

FIG. 3 illustrates in greater detail the steps necessary to produce a display such as illustrated in FIG. 2. For each cardiac cycle, block 301 determines the start and end of the cycle and the number of samples per channel. Reflection coefficients and residual energy for each channel are then determined by blocks 302, 303, and 304. Block 302 performs a autoregressive analysis of the samples for one channel to determine the reflection coefficients and the residual energy. The reflection coefficients define a model constructed by the autoregressive analysis of red blood cell movement. The residual energy is the amount of energy unaccounted for by the model. The reflection coefficients and residual energy are later averaged by blocks 305 and 306 and these averaged coefficients and energies are used to determine the spectrum for each averaged channel by block 307.

After the reflection coefficients and the residual energies have been calculated for all channels of all of the cycles, the average of the reflection coefficients and the residual energy for each particular channel of all of the channels is then calculated by blocks 305 and 306. The result of these averaging calculations is reflection coefficients and energy for each channel which represent the average for that channel over all of the cycles. Once the average of the reflection coefficients and the residual energies for the channels has been computed, the power spectrum of each channel is calculated for a multitude of frequencies utilizing the averaged reflection coefficients and residual energy for this particular channel as calculated in block 305. For each cycle, block 307 and 308 determine the average spectrum for each channel. Once the average spectra for all of the cycles has been calculated, the latter is displayed by block 311 on a color printer which, advantageously, may be Tektronix Corporation's Model 4695 Ink Jet printer. Before display, the average spectra is normalized to take out variations due to the differences of the gain in the Doppler flow meter 102.

Autoregressive spectrum analysis of block 302 assumes an analysis model given by:

$$E(z) = X(z)F(z) \tag{1}$$

where:

E(z) is the z-transform of the input signal,

X(z) is the z-transform of the output signal, and

F(z) is an all pole filter.

In the sample domain, equation 1 can be written as follows:

$$e(n) = \sum_{m=0}^{ORDER} fc(m) \, x(n - m) \quad (2)$$

which can be rewritten as $$e(n) = x(n) - \sum_{m=1}^{ORDER} fc(m) \, x(n - m) \quad (3)$$

where x(n) represents the present time sample, fc represents filter coefficients, and ORDER represents the number of filter elements.

As described in J. D. Markel and A. H. Gray, "Linear Prediction of Speech", Springer-Verlag, Berlin Herdelberg New York, 1980, on page 10, the input signal e(n) can be interpreted as the prediction error between the actual data sample x(n) and the linear combination of the previous n samples given by $$\sum_{m=1}^{M} fc(m) \, x(n - m).$$

since the actual data sample minus the predicted signal can be interpreted as an error, the common analysis procedure is to minimize the sum of the squares of this error as a method for determining the filter coefficients.

Many autoregressive techniques have been developed to minimize this error term; and the one utilized here is the Berg Maximum Entropy method which is described in the paper by L. Marple, "A New Autoregressive Spectrum Analysis Algorithm", IEEE Trans. on Acoustics, Speech, and Signal Processing, Vol. ASSP-28, No. 4, August, 1980, pp. 441–454. The Berg method solves for the filter coefficients, fc(m), by using a forward and backward prediction errors. For any given point, the error is calculated by considering the points in time preceding the sample point under calculations and points prior to the particular point under consideration. The forward error is defined by:

$$f_{err}(k) = \sum_{i=0}^{ORDER} fc(i) * x(k - ORDER - i) \quad (4)$$

while the backward error is defined by:

$$b_{err}(k) = \sum_{i=0}^{ORDER} fc(i) * x(k + i) \quad (5)$$

where the values of index k range from 1 to (NPTS-ORDER) and fc(0) is defined as 1. NPTS is the number of sample points in the channel being analyzed. Using these two expressions, the problem is to determine the set of filter coefficients that minimize the sum of both the forward and backward errors summed over all sample points subject to a constraint. Thus, the error to be minimized is given by the following equation:

$$\text{error} = \sum_{k=1}^{NPTS-ORDER} f_{err}(k) * f_{err}(k) + b_{err}(k) * b_{err}(k). \quad (6)$$

The constraint on the values of fc is that they satisfy the relation $$fc(k) = FC(k) + rc(ORDER) * FC(ORDER - k) \quad (7)$$

where: fc(ORDER) = rc(ORDER).
where FC represents the coefficients determined when ORDER−1 terms were used in the prediction equation. This relation is called the Levinson recursion, and the term, rc(ORDER), is frequently referred to as the LPC reflection coefficient.

The filter coefficients fc(k) can be solved for in equation 6 by substituting equations 4 and 5 into equation 6 and taking the partial derivative of this equation with respect to fc(ORDER). The resulting equation is a recursive formula given in terms of the reflection coefficient as follows:

$$rc(ORDER) = \frac{-2 \sum_{k=1}^{NPTS-ORDER} b_{err}(k) f_{err}(k+1)}{\sum_{k=1}^{NPTS-ORDER} | \, |b_{err}(k)|^2 + |f_{err}(k+1)|^2 \, |} \quad (8)$$

Figure 5:
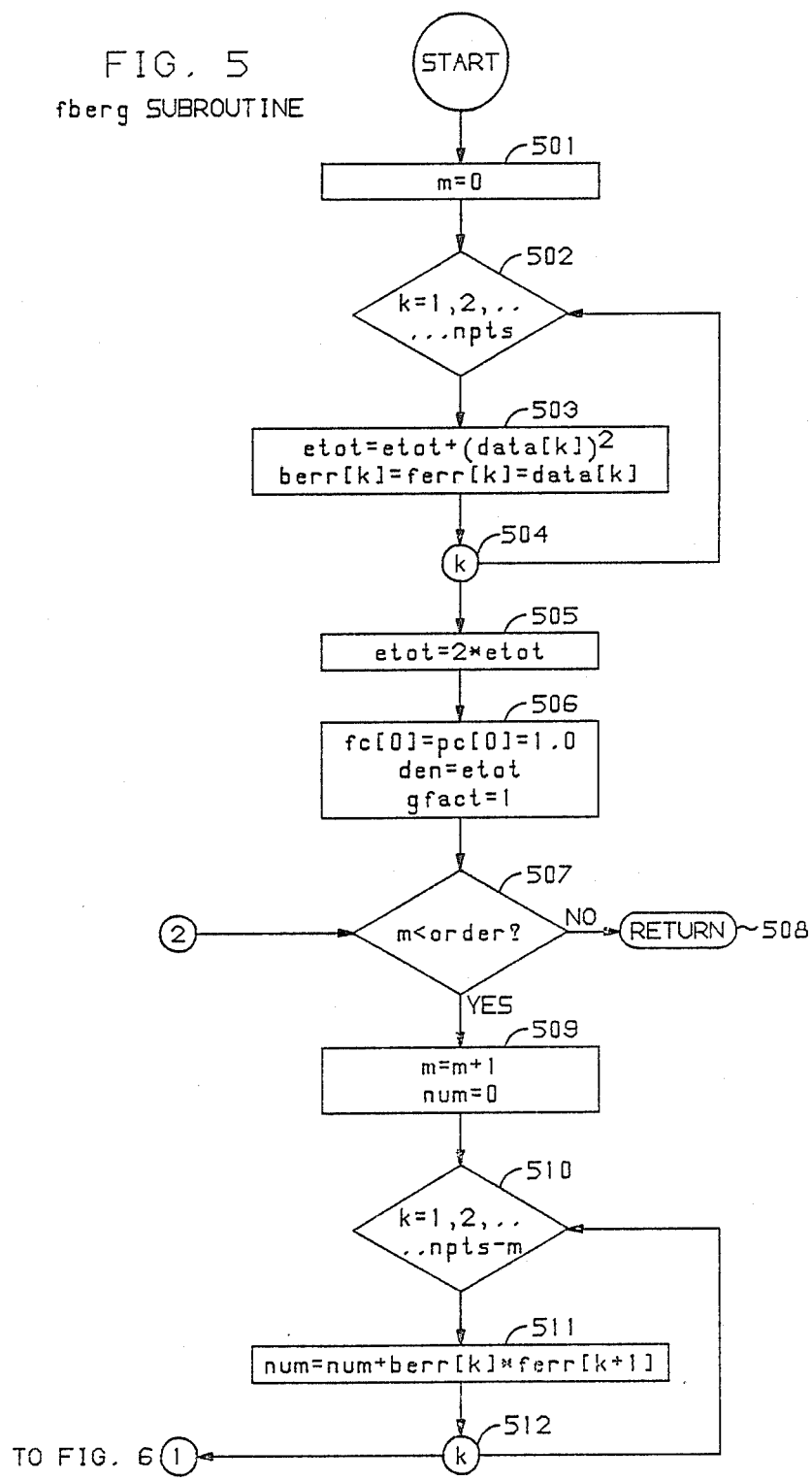
FIGS. 5 and 6 illustrate in greater detail, the program instructions of block 409 of FIG. 4.
Figure 6:
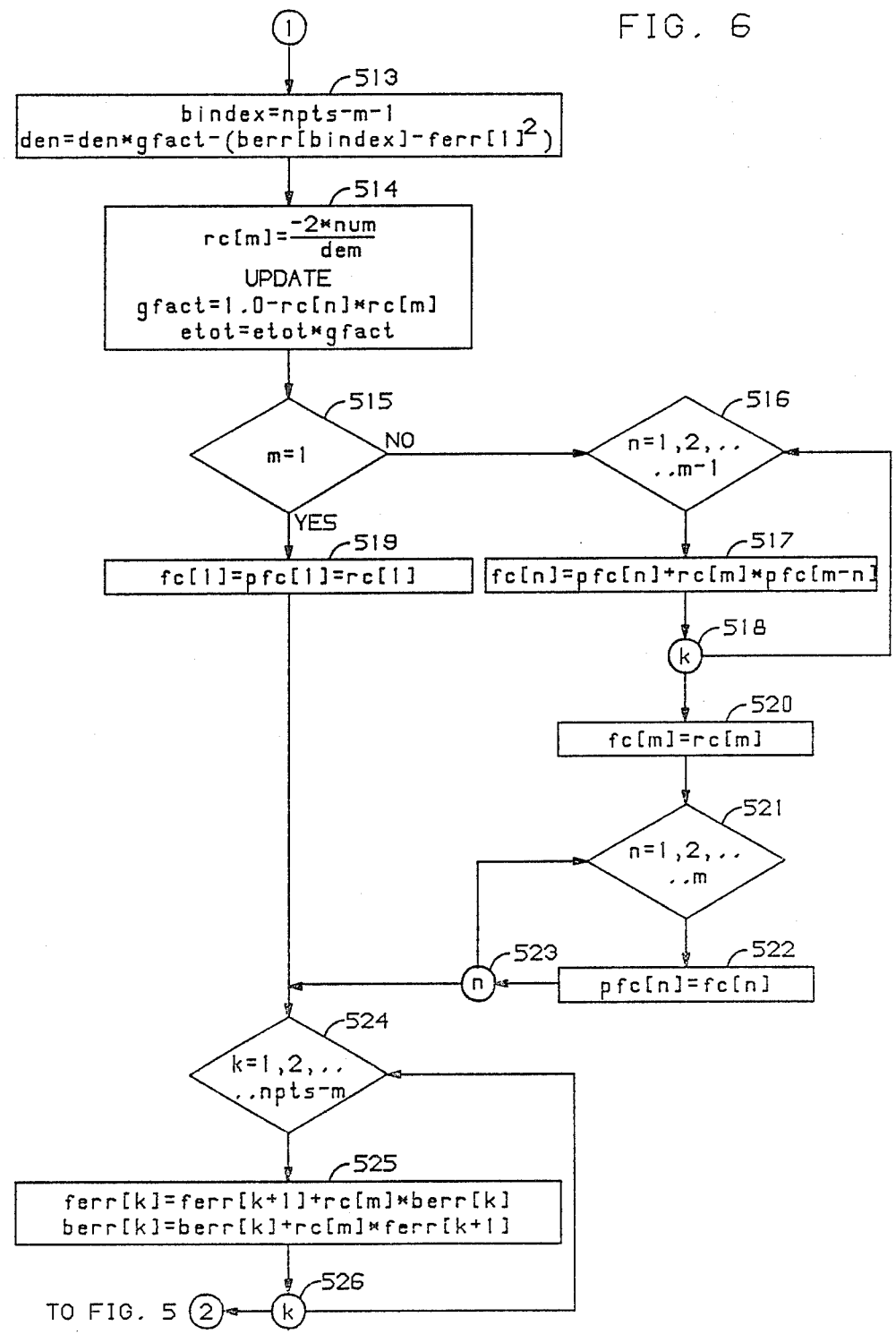

FIGS. 5 through 6 illustrate a program for evaluating equation 8.

Given the filter coefficients, the power spectrum for any frequency, f, is given by $$P(f) = \frac{PE}{ABS \left| 1 + \sum_{k=1}^{ORDER} fc(k) * e^{(-2\pi^* i^* f^* / fsample)} \right|^2} \quad (9)$$

where fsample is the frequency at which the original signal was sampled, P(f) is the power at the particular frequency f, and PE is a measure of the residual energy left over in the autoregressive analysis. ABS represents the magnitude function of a complex number.

The programs illustrated in later material by flowcharts and program listings require equation 9 to be transformed to equation 10 for the following reasons. The power is computed in db to avoid large numbers. Thus, log (P(f)) is the quantity calculated. Also, since the programs are written in the C programming language, which does not have complex arithmetic, the exponential factor is broken down into real and imaginary parts. For these reasons, equation 9 is transformed into the following:

$$10*\log(P(f)) = 10*\log(PE) - 20*\log(ABS) \quad (10)$$

$$\left| 1 + \sum_{k=1}^{ORDER} fc(k) * \{ \cos(k*f*arg) + i*\sin(k*f*arg) \} \right|$$

where arg = 2*π/fsample.
The equations 4 through 10 give a mathematical description of the process required to implement the flowchart of FIG. 3.

Figure 4:
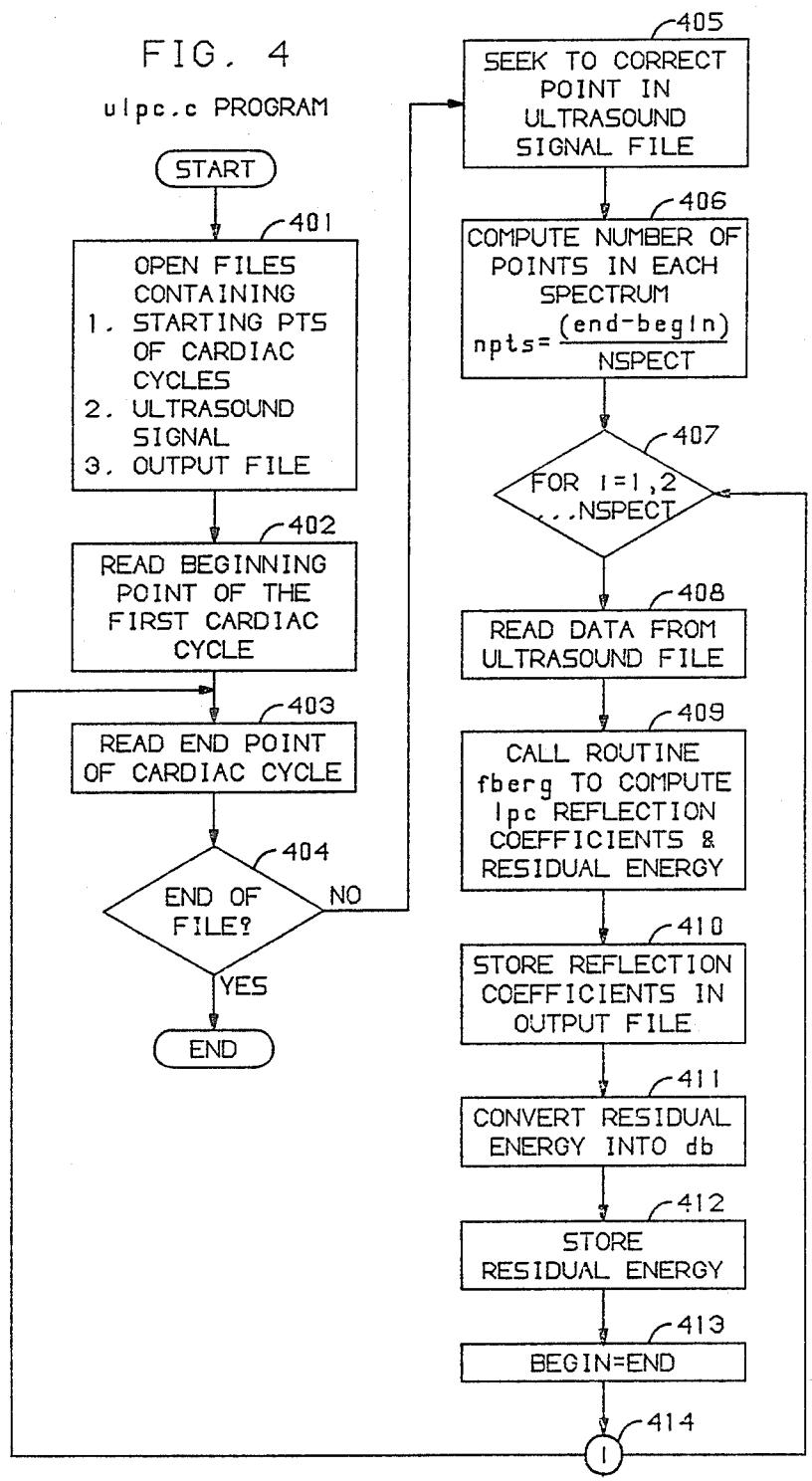
FIG. 4 is a detailed flowchart of the program steps executed by blocks 302 through 304 of FIG. 3.

Now consider in greater detail, the various programs that are required to perform the previous equations. The process of performing the autoregressive analysis, as defined in block 302 of FIG. 3, is shown in greater detail in the flowchart illustrated in FIG. 4 and in Appendix A as routine ulpc.c. As illustrated in FIG. 4, the program first opens the necessary files, block 401, in order to gain access to the digitized Doppler signal and the points which define the start and end of the cardiac cycles. Block 402 first reads the beginning of the first cycle and blocks 403 and 404 checks if the entire file has been read. If the entire file has been read, then the program is finished. However, if the entire file has not been read, block 405 utilizes the starting point of the cardiac cycle to seek to the proper place in the Doppler signal file. Block 406 then computes the number of sample points for each channel by dividing the total number of samples by the number of channels. Illustratively, the number of channels is 50. Blocks 407 through 414 then compute the reflection coefficients and residual energy for a particular channel. For each channel, the data samples of that channel are utilized to calculate the reflection coefficients and the residual energy in block 409. The latter block implements the Berg method by utilizing subroutine fberg which is illustrated in FIGS. 5 through 6 and a program listing is given in Appendix B. The reflection coefficients are then stored in an output file by block 410. The reason for storing reflection coefficients rather than the filter coefficients themselves is that the reflection coefficients are bounded between 1 and −1 whereas the filter coefficients can be quite larger or small. The residual energy is converted to db and stored by blocks 411 and 412. Blocks 413 and 414 determine whether or not all the points of the channel have been utilized. If they have, then the program returns to block 403 to process another cycle.

The fberg subroutine is illustrated in greater detail in FIGS. 5 and 6. This subroutine calculates equation 8 and verifies that the conditions of equation 7 have been met. The fberg routine calculates equation 8 in a recursive manner by first calculating the first reflection filter coefficient for order 1 and then uses this information to calculate a new set of filter coefficients for order 2. Because of this recursive nature, fberg routine is repetitively recalculating equation 8. Blocks 501 through 506, illustrated on FIG. 5, perform the initialization of the various variables used by the subroutine. The initial residual energy, etot, is set equal to the sum of the squares of all the data points of the channel and the backward and forward errors (berr and ferr, respectively) are set equal to corresponding data samples, where the data sample is the digitized Doppler signal. The filter coefficients are initially set equal to 1 by block 506 and the denominator of equation 8 is set equal to the initial residual energy as determined by block 503.

FIGS. 5 and 6 illustrate the evaluation of equation 8. Block 507 determines whether or not the equation has been sufficiently evaluated for the order filter being calculated, and if it has, a return is executed to the program illustrated on FIG. 4 via return block 508. If the filter has not yet been calculated to a sufficient order, then block 509 is executed. The numerator and denominator (num and den, respectively) of equation 8 for this particular order are evaluated by blocks 510 through 513. After the numerator and denominator have been determined, then the reflection coefficient, rc[m], and residual energy for this particular order are evaluated in block 514. Once the reflection coefficient for this order has been determined, then the stepup function is implemented by blocks 515 through 519 to update the previously determined filter coefficients for (ORDER −1) as defined by the Levinson recursion formula and given in equation 7. The highest order filter coefficient is always equal to the reflection coefficient and is set equal to the reflection coefficient by block 520. The past filter coefficients are then updated by blocks 521 through 523 in order for block 517 to evaluate the next set of filter coefficients. The past filter coefficients are designated as FC(n) in equation 7, and as pfc[n] on FIGS. 5 and 6. The forward and backward errors are next updated by blocks 524 through 526 in order to evaluate blocks 511 and 513 in the next iteration. After the forward and backward errors have been updated, control is passed from block 526 to decision block 507 which determines whether or not all the orders have been evaluated.

Referring back to FIG. 3, after the reflection coefficients and residual energy levels have been calculated in blocks 302 through 304, the average for each individual channel over all cycles is performed as illustrated in blocks 305 and 306. Again, referring back to FIG. 3, once the averaging has been performed by blocks 305 through 306, the power spectrum for each channel is calculated for a plurality of frequencies as defined in equation 10. Illustratively, for each channel, equation 10 is evaluated for 150 different frequencies by blocks 307 and 308. After the average power spectra has been calculated for the cycles, the resulting power spectra is normalized by block 310 and then displayed by block 311.

Figure 7:
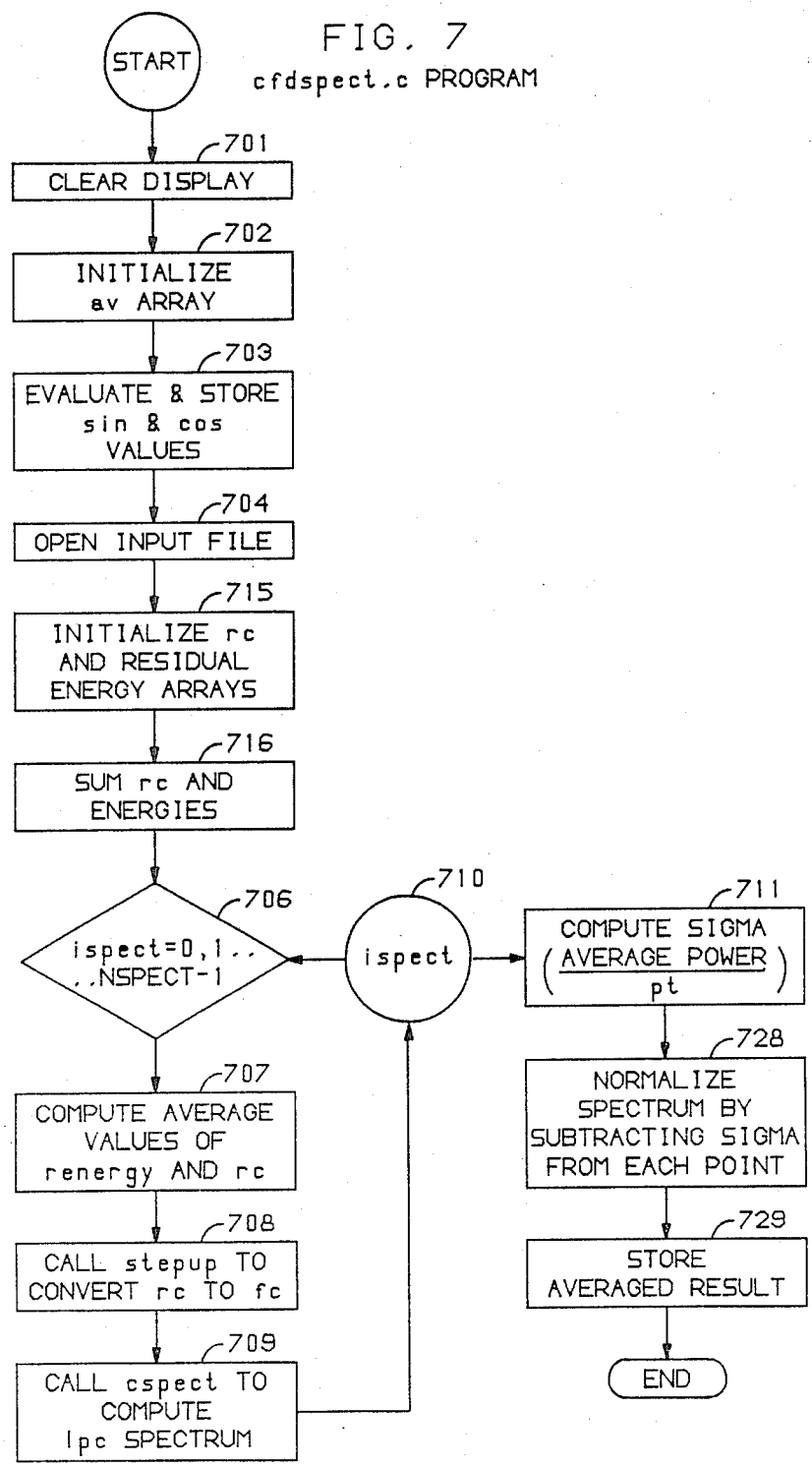
FIG. 7 is a detailed flowchart of blocks 307 through 310.

Blocks 305 through 310 are implemented by the cfdspect.c program which is illustrated as a flowchart in FIG. 7 and in source code form in Appendix C. Blocks 701 through 704 perform the initialization required for the execution of the cfdspect.c program. The sine and cosine values of equation 10 are initially evaluated and stored so as to save processing time. The av array which is used to hold the averages for the spectra for the different channels is initialized to 0. Next, the arrays which hold the values for the reflection coefficients and the residual energy levels for all the channels of all the cycles are initialized by block 715 reading this information from a file created by blocks 410 and 412 of FIG. 4. Next, block 716 sums the reflection coefficients and residual energy level for each particular channel for all cycles with reflection coefficients for the same filter element being summed together for all cycles.

Figure 8:
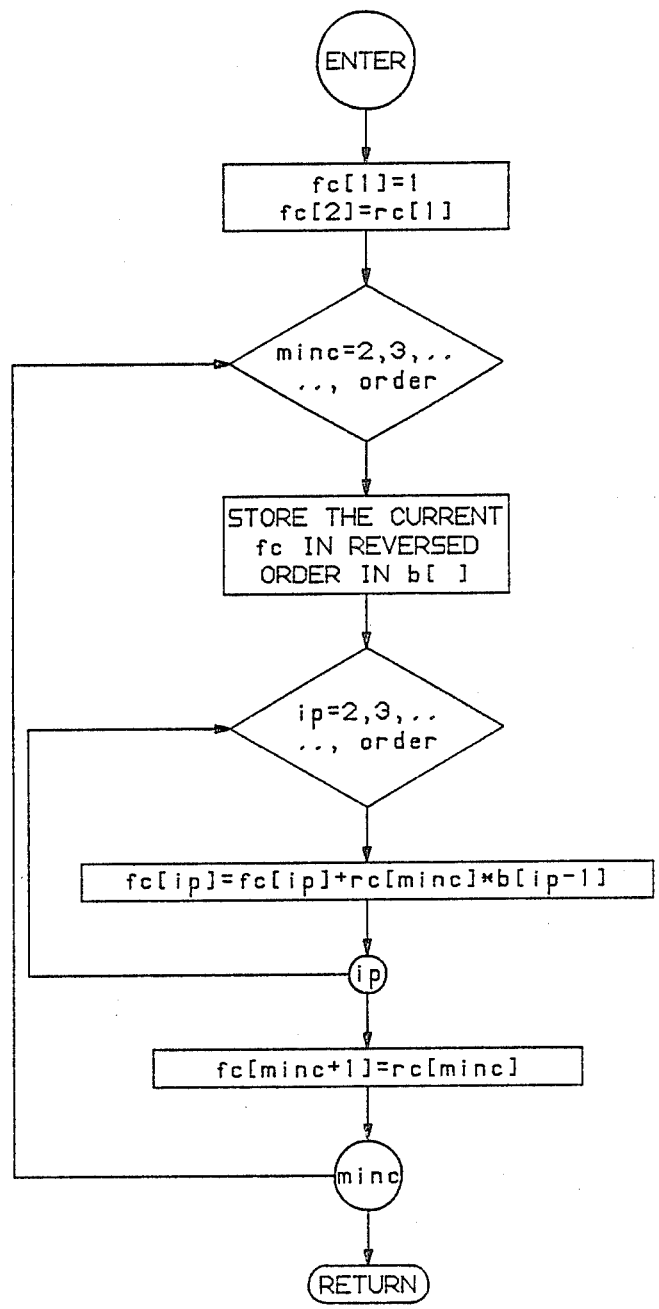
FIG. 8 is a detailed flowchart of block 708 of FIG. 7.
Figure 9:
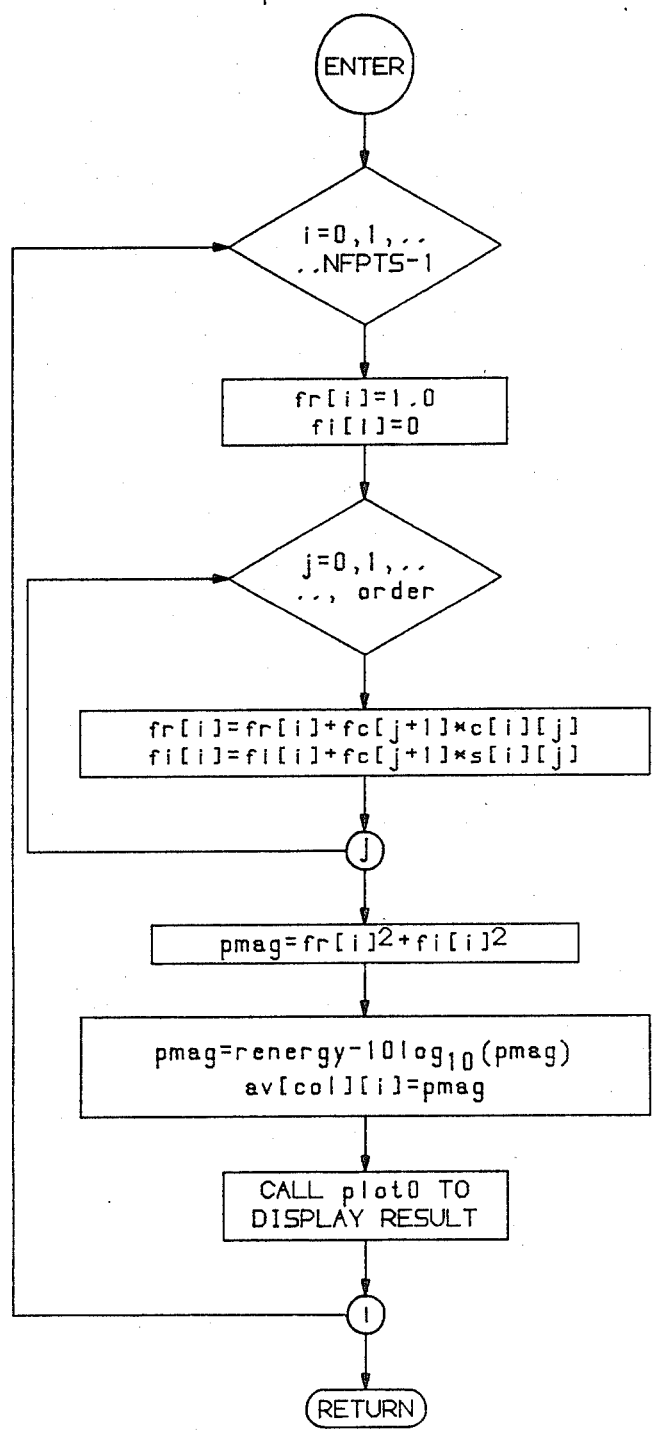
FIG. 9 is a detailed flowchart of block 709 of FIG. 7.

After the reflection coefficients and residual energy levels have been summed for all cycles, the power spectrum for each combined channel is calculated by blocks 706 through 710 in the following manner. For each combined channel, the average of the reflection coefficients and the residual energy level is calculated by block 707. Block 708 then converts the reflection coefficients for the channel into filter coefficients by executing the stepup subroutine that implements equation 7. This subroutine is illustrated in FIG. 8. Once the filter coefficients have been calculated, the power spectrum is calculated by block 709 which uses the cspect subroutine of FIG. 10. Blocks 706 and 710 control the program flow so that the previous calculations are performed for all of the combined channels.

Once the spectra for all of the combined channels has been calculated, then blocks 711, 728, and 729 are executed implementing block 310 of FIG. 3 which normalizes and stores the resulting spectra of all of the cycles. The normalized spectra are displayed on a color printer such as Tektronix Corporation, Model 4695. A program for performing the display of the normalized spectra is the tekcopy program which is listed in Appendix D.

A program for performing the determination of the start and end of each cycle as shown in block 301 of FIG. 3 is illustrated in program form in Appendix E. Further explanation of this program is given in the copending application of Prezas, et al.

It is to be understood that the above-described embodiment is merely illustrative of the principles of this invention; other arrangements may be devised by those skilled in the art without departing from the spirit and the scope of the invention.

What is claimed is:

1. An autoregressive analysis system for obtaining the average power spectrum of a plurality of signal groups each comprising a plurality of information signals, comprising:
    means for determining the start and end of each of said signal groups;
    means responsive to said information signals of each of said groups as determined by said determining means for calculating reflection coefficients for each of said signal groups;
    means responsive to said information signals and said reflection coefficients for each of said signal groups for generating a residual energy level for each of said signal groups;
    means for averaging said reflection coefficients of said signal groups and said residual energy levels of said signal groups; and
    means responsive to said averaged reflection coefficients and said averaged residual energy level for generating the average power spectrum.

2. The system of claim 1 further comprising means for transmitting a beam of ultrasonic frequency acoustic signals into an internal patient vessel;
    means for receiving the reflected acoustic echoed signals from moving blood cells in said internal patient vessel;
    means for determining the difference between said transmitted and said received signals; and
    means for sampling said difference signals to determine said information signals of said signal groups.

3. The system of claim 2 wherein said means for determining said start and end of each of said signal groups comprises:
    means for obtaining said patient's electrocardiogram signals; and
    means for designating said start and end of said signal groups corresponding to cardiac cycles in response to said patient's electrocardiogram signals.

4. The system of claim 3 wherein said calculating means comprises:
    means for computing a forward error for each of said information signals of each of said signal groups representing the difference between each of said information signals and subsequent ones of said information signals for each of said signal groups;
    means for computing a backward error signal for each of said information signals of each of said signal groups representing the difference between each of said information signals and the preceding information signals for each of said signal groups; and
    means for computing reflection coefficients in response to said backward and forward error signals for each of said signal groups.

5. A blood flow analysis system for measuring velocity of blood moving within a patient's internal structures, comprising:
    means for transmitting a beam of ultrasonic frequency acoustic waves into said patient structures;
    means for receiving the reflected acoustical echoed signals from moving acoustic scatterers in said blood;
    means for determining signals representing the difference between said transmitted and said received signals;
    means for sampling said difference signals for a plurality of cardiac cycles;
    means for determining the start and end of each of the patient's cardiac cycles in response to electrocardiogram signals from said patient;
    means responsive to said start and end of each of said cardiac cycles and said sampled difference signals for each individual cardiac cycle for dividing said sampled difference signals into a predefined number of time segments of signals each representing the same amount of time with the total amount of time equal to each individual cardiac cycle;
    means responsive to said sampled difference signals for each of said time segments for calculating reflection coefficients modeling said blood flow;
    means responsive to said sampled difference signals and said reflection coefficients for generating a residual energy level for each of said time segments representing the energy not accounted for by said modeling;
    means responsive to said residual energy level and said reflection coefficients for each individual time segment of all cardiac cycles for averaging said reflection coefficients and said residual energy levels; and
    means responsive to said averaged reflection coefficients and said averaged residual energy level of each individual time segment for determining the average power spectrum of each individual time segment.

6. The system of claim 5 further comprises means for displaying said averaged power spectrum for each individual time segment with difference colors representing different power levels.

7. The system of claim 6 further comprising means for storing said averaged reflection coefficients and residual energy levels for all of said individual time segments for later analysis.

8. The system of claim 7 further comprising means for redetermining said averaged power spectrum for each of said combined time segments from the stored average reflection coefficients and the stored residual energy levels for displaying said redetermined average power spectrum for each individual time segment with different colors representing different power levels.

9. The system of claim 7 wherein said means for calculating said reflection coefficients comprises:
    means for computing a forward error signal for each of said sampled difference signals for each time segment representing the difference between each of said sampled difference signals and subsequent ones of said sampled difference signals of the same segment;
    means for computing a backward error signal for each of said sampled difference signals of each channel representing the difference between each of said sampled difference signals and preceding sampled difference signals of the same channel; and
    means for computing reflection coefficients in response to said backward and forward error signals for each of said time segments.

10. The system of claim 6 wherein said displaying means comprises means for normalizing said average power spectrum for each of said combined time segments before display.

11. The system of claim 5 wherein said reflection coefficient calculating means implements the Berg technique for generating said reflection coefficients and residual energy levels.

12. A blood flow analysis system for measuring the velocity of blood moving within internal patient vessels, comprising:
   means for transmitting a beam of ultrasonic frequency acoustic signals into said patient vessels for a plurality of cardiac cycles;
   means for receiving the reflected acoustic echoed signals from moving blood cells in said blood vessels over said plurality of cardiac cycles;
   means for determining signals representing the difference between said transmitted and received signals;
   means for sampling the difference signals;
   a first set of program instructions for determining the start and end of each of said cardiac cycles in response to said patient's electrocardiogram signals;
   a second set of program instructions responsive to said start and end of each of said plurality of cardiac cycles and said corresponding sampled difference signals of each of said plurality of cardiac cycles for dividing said corresponding sampled difference signals into a predefined number of channels of said sampled difference signals for each of said plurality of cardiac cycles with each channel representing the same amount of time with the total amount of time of all channels of a particular cardiac cycle equal to that cardiac cycle;
   a third set of program instructions responsive to said sampled difference signals of each of said channels for generating reflection coefficients for modeling the amount of blood movement for all of said cycles;
   a fourth set of program instructions responsive to said reflection coefficients and said sampled difference signals for each of said channels for all of said cardiac cycles for generating a residual energy level for each of said channels representing energy not accounted for by said modeling;
   a fifth set of program instructions responsive to said reflection coefficients for a particular channel for all cardiac cycles for determining the average of said reflection coefficients for said particular channel for all of said cardiac cycles;
   a sixth set of program instructions responsive to said residual energy level for a particular channel for all cycles for determining the average of said residual energy levels for said particular channel for all of said cardiac cycles;
   a seventh set of program instructions for calculating the total energy of all sampled difference signals for each particular channel for all of said cardiac cycles;
   a eighth set of program instructions for calculating the average energy spectrum from said averaged reflection coefficients and average residual energy level for each of the averaged channels;
   an ninth set of program instructions for dividing the averaged power spectrum by said total energy for each of said averaged channels to produce a normalized power spectrum for each averaged channel; and
   a tenth set of program instructions responsive to normalized power spectrum for displaying said normalized power spectrum for each of said averaged channels.

13. The system of claim 12 wherein said third set of program instructions comprises:
   a first subset of program instructions for computing a forward error signal for each of said sampled difference signals for each channel representing the difference between each of said sampled signals and the subsequent ones of said sampled difference signals of the same channel;
   a second subset of program instructions for computing a backward error signal for each of said sampled difference signals and the preceding sampled difference signals of the same channel; and
   a third subset of program instructions for computing reflection coefficients in response to said backward and forward error signals for each of said channels.

14. A method for measuring blood flow within internal blood vessel of a patient by analyzing sampled reflected ultrasonic signals from moving blood cells within the vessels during cardiac cycles and electrocardiogram signals received from said patient, comprising the steps of:
   determining the start and end of aid patient's cardiac cycles in response to said electrocardiogram signals;
   dividing said sampled reflected ultrasonic signals up into a predefined number of time channels for each of said cardiac cycles with the total of said time channels corresponding to that one of said cardiac cycles;
   calculating reflection coefficients modeling said blood flow in response to said sampled reflected ultrasonic signals for each channel for all of said cardiac cycles;
   computing a residual energy level for each of said time channels of all cardiac cycles representing the energy not accounted for by said modeling;
   averaging said reflection coefficients and said residual energy levels for each individual time channel of all cardiac cycles; and
   determining the average power spectrum of each of the combined time channels in response to the average reflection coefficients and the average residual energy level for each of said combined time channels.

15. The method of claim 14 further comprises the step of displaying said average power spectrum for each of said combined time segments with different colors representing different power levels.

16. The method of claim 15 wherein said step of displaying further comprises the step of normalizing said average power spectrum for each of said combined time channels before displaying the latter.

17. The invention of claim 14 wherein said calculating step comprises the steps of:
   computing a forward error signal for each of said sampled reflected ultrasonic signals for each time channel representing the difference between each of said sampled reflected ultrasonic signals and subsequent ones of said sampled ultrasonic signals of the same channel;
   computing backward error signals for each of said sampled reflected ultrasonic signals of each channel representing the difference between each of said sampled ultrasonic signals and preceding sampled ultrasonic signals of the same channel; and
   computing reflection coefficients in response to said backward and forward error signals for each of said time channels.

* * * * *